(12) United States Patent  (10) Patent No.: US 9,261,436 B2
Ono  (45) Date of Patent: Feb. 16, 2016

(54) FLUID TREATMENT DEVICE AND METHOD FOR TREATING FLUID

(75) Inventor: Koichi Ono, Saitama (JP)

(73) Assignee: Enplas Corporation, Saitama (JP)

( * ) Notice: Subject to any disclaimer, the term of this patent is extended or adjusted under 35 U.S.C. 154(b) by 87 days.

(21) Appl. No.: 14/234,686

(22) PCT Filed: Jul. 23, 2012

(86) PCT No.: PCT/JP2012/004651
§ 371 (c)(1),
(2), (4) Date: Jan. 24, 2014

(87) PCT Pub. No.: WO2013/014905
PCT Pub. Date: Jan. 31, 2013

(65) Prior Publication Data
US 2014/0174161 A1  Jun. 26, 2014

(30) Foreign Application Priority Data

Jul. 25, 2011  (JP) .................................. 2011-161914
Jul. 19, 2012  (JP) .................................. 2012-160407

(51) Int. Cl.
*F16K 7/17* (2006.01)
*G01N 1/10* (2006.01)
(Continued)

(52) U.S. Cl.
CPC . *G01N 1/10* (2013.01); *B01J 19/00* (2013.01); *B01L 3/502738* (2013.01); *F16K 7/17* (2013.01); *B01L 3/502707* (2013.01); *B01L 2300/0816* (2013.01); *B01L 2300/123* (2013.01);
(Continued)

(58) Field of Classification Search
CPC .................... B01L 3/502738; B01L 3/502707; B01L 2300/123; B01L 2300/0816; B01L 2400/0487; B01L 2400/0655; G01N 1/10; F16K 7/17; F16K 99/0015; F16K 99/0055; F16K 99/0011; B01J 19/00
USPC ................................ 137/599.04–599.07, 863
See application file for complete search history.

(56) References Cited

U.S. PATENT DOCUMENTS 3,318,329 A * 5/1967 Norwood ................. 137/601.13
3,433,257 A   3/1969 Jensen
(Continued)

FOREIGN PATENT DOCUMENTS

FR  2235301 A1  1/1975
JP  2002-228033 A  8/2002
(Continued)

OTHER PUBLICATIONS

Extended European Search Report dated Apr. 7, 2015 for the corresponding European Patent Application No. 12816989.3.

*Primary Examiner* — Marina Tietjen
(74) *Attorney, Agent, or Firm* — Brundidge & Stanger, P.C.

(57) ABSTRACT

A fluid treatment device (100) has a first substrate (210), a second substrate (120), and a resin film (130) located between the first substrate (210) and the second substrate (120). On the first substrate (210) are formed a first flow channel (111), a region (214) facing a valve formed at the end of the first flow channel (111), a second flow channel (112), and a barrier wall (215) located between the region (214) facing the valve and the end of the second flow channel (112). On the second substrate (120) is formed a pressure compartment (123). The region (214) facing the valve and the barrier wall (215) face the pressure compartment (123) on opposite sides of a diaphragm (131) of resin film (130).

6 Claims, 13 Drawing Sheets

(51) Int. Cl.
　　　*B01J 19/00*　　　(2006.01)
　　　*B01L 3/00*　　　(2006.01)

(52) U.S. Cl.
　　　CPC .. *B01L2400/0487* (2013.01); *B01L 2400/0655* (2013.01)

(56) References Cited

U.S. PATENT DOCUMENTS

| | | | |
|---|---|---|---|
| 3,610,274 A | 10/1971 | Levesque et al. | |
| 4,858,883 A * | 8/1989 | Webster | 251/61.1 |
| 8,057,629 B2 | 11/2011 | Zhou et al. | |
| 8,945,484 B2 * | 2/2015 | Namkoong et al. | 422/537 |
| 2004/0209354 A1 * | 10/2004 | Mathies et al. | 435/287.2 |
| 2005/0019794 A1 | 1/2005 | Nassef et al. | |
| 2006/0076068 A1 | 4/2006 | Young et al. | |
| 2006/0078470 A1 | 4/2006 | Zhou et al. | |
| 2008/0178987 A1 | 7/2008 | Zhou et al. | |
| 2010/0266432 A1 * | 10/2010 | Pirk et al. | 417/472 |
| 2011/0041935 A1 | 2/2011 | Zhou et al. | |

FOREIGN PATENT DOCUMENTS

| | | |
|---|---|---|
| JP | 3418727 B2 | 6/2003 |
| JP | 2004-033919 A | 2/2004 |
| JP | 2009-510337 A | 3/2009 |
| JP | 2009-236555 A | 10/2009 |
| JP | 2010-107050 A | 5/2010 |
| WO | 02/41994 A2 | 5/2002 |
| WO | 2008/115626 A2 | 9/2008 |

* cited by examiner

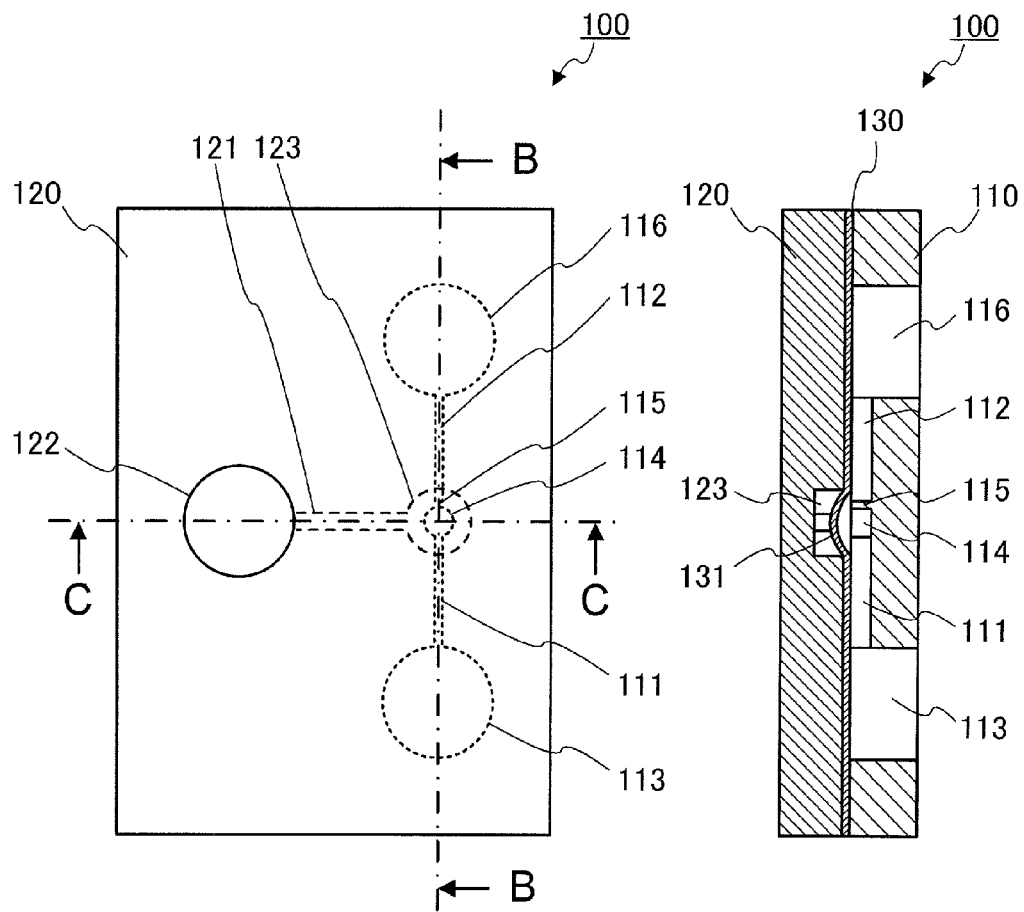
FIG. 1A
FIG. 1B
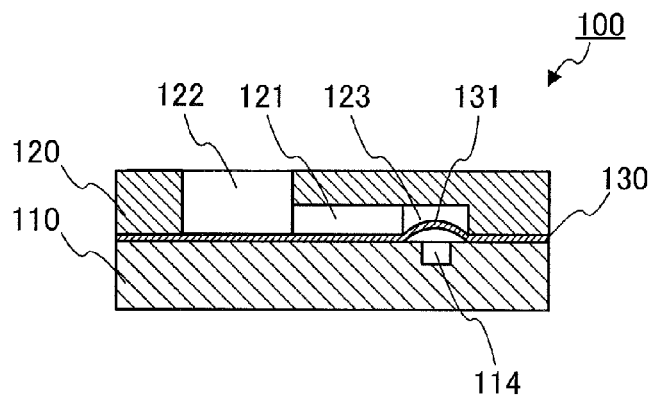
FIG. 1C

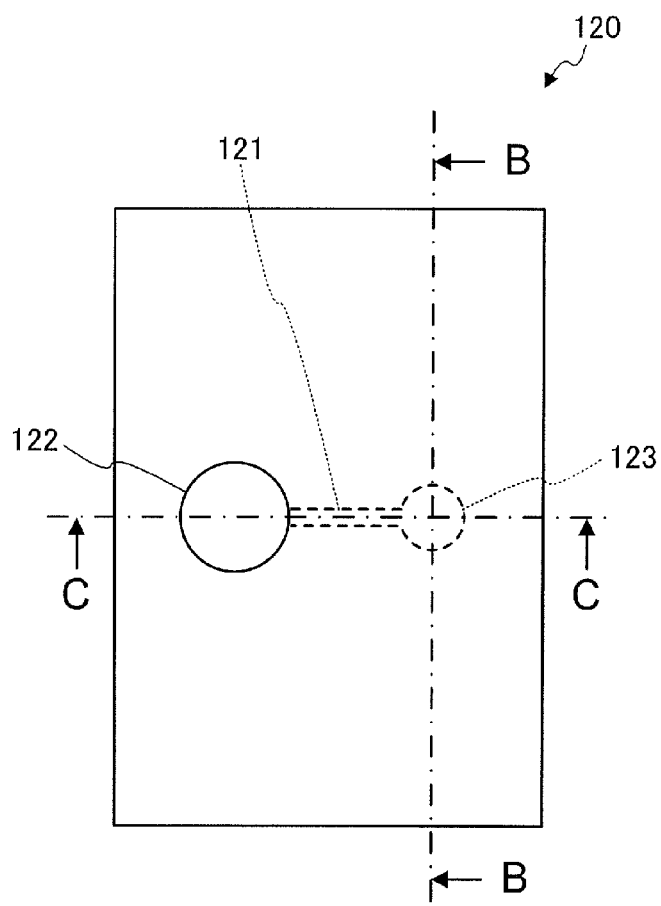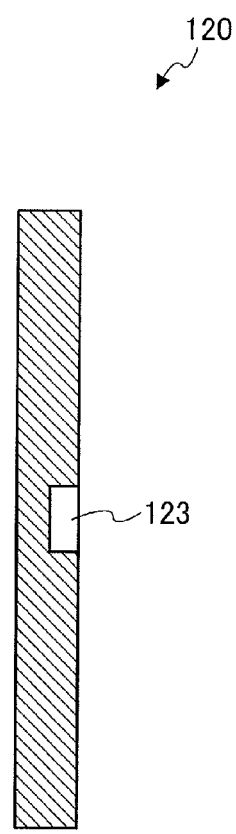
FIG. 3A  FIG. 3B
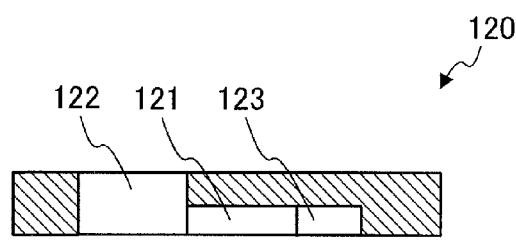
FIG. 3C

FLUID TREATMENT DEVICE AND METHOD FOR TREATING FLUID

TECHNICAL FIELD

The present invention relates to a fluid handling device and a fluid handling method which are used for analysis or processing of a liquid sample, or the like.

BACKGROUND ART

In recent years, in order to perform analysis of trace amounts of substances such as proteins or nucleic acids with high accuracy and at high speed, microchannel chips have been used. The microchannel chips have an advantage of requiring smaller amounts of reagents and samples and thus are expected to be used in various applications including clinical inspection, food inspection, and environmental inspection.

In order to automate processing using the microchannel chip, providing a valve structure in the microchannel chip is proposed (refer to PTL 1, for example).

PTL 1 discloses a microchannel chip having a microvalve of a diaphragm valve structure which opens and closes a channel by changing the shape of a side wall of the channel. In the microchannel chip, a second channel is formed in the vicinity of a first channel. When pressure of a fluid in the second channel is increased, a wall (a diaphragm) of the first channel, which is located between the first channel and the second channel, is deformed so as to block the first channel. Therefore, the fluid flow in the first channel can be controlled by adjusting pressure to a fluid in the second channel.

CITATION LIST

Patent Literature

PTL 1
US Patent Application Publication No. 2005/0019794

SUMMARY OF INVENTION

Technical Problem

However, the microchannel chip described in PTL 1 has the disadvantage of high manufacturing cost. With the technique described in PTL 1, in order to make the wall (diaphragm) of the first channel have elasticity, the entire microchannel chip is made of an expensive elastomer (e.g.; polydimethylsiloxane (PDMS)). For this reason, with the technique described in PTL 1, it is difficult to manufacture a microchannel chip at a low cost.

As means for suppressing the manufacturing cost, it is conceivable to manufacture a microchannel chip by using resin. However, when manufacturing a diaphragm by using a resin film having a certain level of thickness, since resin has high rigidity compared to an elastomer, it is difficult to completely block a channel by a resin film (diaphragm). That is, after a portion of the resin film (diaphragm) comes into contact with a channel, in order to bring the remainder of the diaphragm into contact with the channel, it is necessary to apply a very large amount of pressure.

An object of the present invention is to provide a fluid handling device of low manufacturing costs that allows for easy control of fluid flow in a channel, and a fluid handling method using the fluid handling device.

Solution to Problem

A fluid handling device according to the invention includes: a first substrate which includes a first channel, a valve body facing area formed at an end on one side of the first channel and having a substantially circular segment-shaped opening, a second channel, and a partition wall formed between the valve body facing area and an end on one side of the second channel; a second substrate which includes a third channel and a pressure chamber formed at an end on one side of the third channel and having an opening; and a resin film which is disposed between the first substrate and the second substrate and includes a substantially spherical cap-shaped diaphragm portion, in which the first substrate and the second substrate are integrated with each other with the resin film in between, the diaphragm portion is located between the opening of the valve body facing area, the end on one side of the second channel and the partition wall, and the opening of the pressure chamber, a center of a circular arc which is included in an edge of the opening of the valve body facing area and a center of an outer edge of the diaphragm portion coincide with each other when seen in a plan view, and the diaphragm portion comes into contact with the partition wall due to pressure in the pressure chamber, whereby fluid flow heading for the second channel from the valve body facing area through a gap between the partition wall and the diaphragm portion is stopped.

A fluid handling device according to the invention includes: a first substrate which includes a first channel, a valve body facing area formed at an end on one side of the first channel and having a substantially circular opening, a second channel, and a partition wall formed between the valve body facing area and an end on one side of the second channel; a second substrate which includes a third channel and a pressure chamber formed at an end on one side of the third channel and having an opening; and a resin film which is disposed between the first substrate and the second substrate and includes a substantially spherical cap-shaped diaphragm portion, in which the first substrate and the second substrate are integrated with each other with the resin film in between, the diaphragm portion is located between the opening of the valve body facing area, the end on one side of the second channel and the partition wall, and the opening of the pressure chamber, and when seen in a plan view, the diaphragm portion is larger than the opening of the valve body facing area and an edge of the opening of the valve body facing area and an outer edge of the diaphragm portion of the resin film are concentric circles, and the diaphragm portion comes into contact with the partition wall due to pressure in the pressure chamber, whereby fluid flow heading for the second channel from the valve body facing area through a gap between the partition wall and the diaphragm portion is stopped.

A fluid handling method according to the invention is a method of handling a fluid by using the fluid handling device described above, including: a step of introducing a first fluid into the first channel to move the first fluid from the first channel through a gap between the partition wall and the diaphragm portion to the second channel; and a step of stopping the first fluid flow by introducing a second fluid into the pressure chamber through the third channel and thus bringing the diaphragm portion into contact with the partition wall due to pressure of the second fluid in the pressure chamber.

Advantageous Effects of Invention

According to the invention, it is possible to provide a fluid handling device of low manufacturing costs that allows for easy control of fluid flow in a channel, and a fluid handling method using the fluid handling device.

BRIEF DESCRIPTION OF DRAWINGS

FIG. 1A is a plan view of a microchannel chip according to Embodiment 1, FIG. 1B is a cross-sectional view taken along line B-B shown in FIG. 1A, and FIG. 1C is a cross-sectional view taken along line C-C shown in FIG. 1A;

FIG. 3A is a plan view of a second substrate, FIG. 3B is a cross-sectional view taken along line B-B shown in FIG. 3A, and FIG. 3C is a cross-sectional view taken along line C-C shown in FIG. 3A;

DESCRIPTION OF EMBODIMENTS

Hereinafter, embodiments of the invention will be described in detail with reference to the drawings. In the following description, as a representative example of a fluid handling device according to the invention, a microchannel chip will be described.

Embodiment 1

Configuration of Microchannel Chip

FIGS. 1A to 1C are diagrams showing the configuration of microchannel chip 100 according to Embodiment 1. FIG. 1A is a plan view of microchannel chip 100, FIG. 1B is a cross-sectional view taken along line B-B shown in FIG. 1A, and FIG. 1C is a cross-sectional view taken along line C-C shown in FIG. 1A.

As shown in FIGS. 1A to 1C, microchannel chip 100 has first substrate 110, second substrate 120, and resin film 130 disposed between first substrate 110 and second substrate 120. A channel for making a fluid such as a reagent or a liquid sample flow therein is formed in first substrate 110. On the other hand, resin film 130 functions as a diaphragm (a valve body) of a microvalve which controls the fluid flow flowing in the channel. A pressure chamber for controlling an operation of the diaphragm is formed in second substrate 120. First substrate 110 and second substrate 120 are integrated with each other through resin film 130.

Hereinafter, each constituent element of microchannel chip 100 will be described.

(First Substrate)

Figures 2A, 2B:
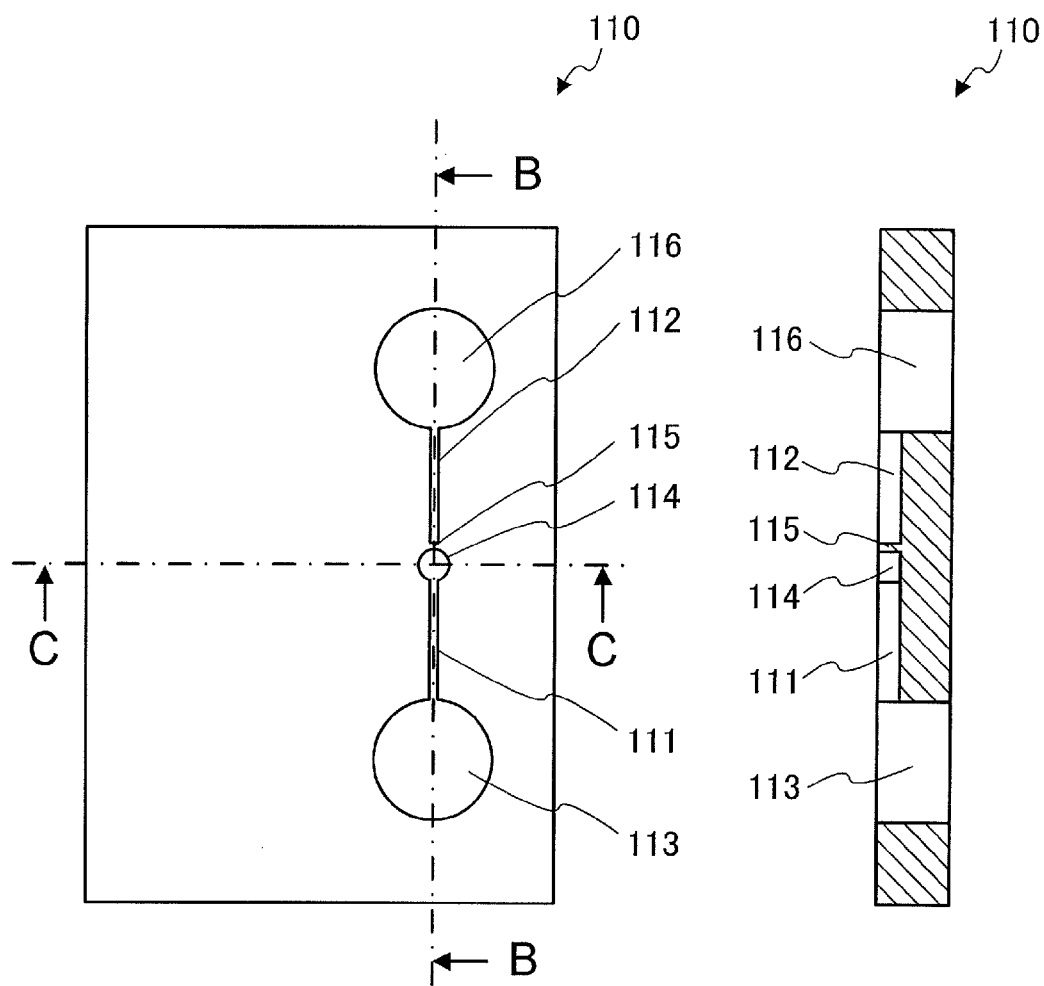
FIG. 2A is a plan view of a first substrate.
FIG. 2B is a cross-sectional view taken along line B-B shown in FIG. 2A.
Figure 2C:
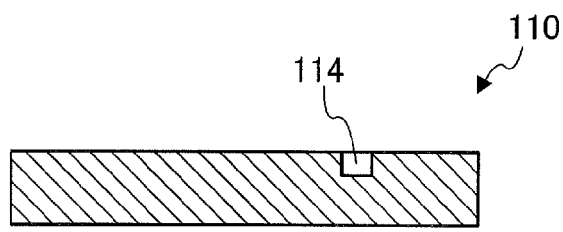
FIG. 2C is a cross-sectional view taken along line C-C shown in FIG. 2A.

FIGS. 2A to 2C are diagrams showing the configuration of first substrate 110. FIG. 2A is a plan view of first substrate 110, FIG. 2B is a cross-sectional view taken along line B-B shown in FIG. 2A, and FIG. 2C is a cross-sectional view taken along line C-C shown in FIG. 2A.

First substrate 110 is a substantially rectangular transparent resin substrate. The thickness of first substrate 110 is not particularly limited. The thickness is, for example, in a range of 1 mm to 10 mm. The type of resin configuring first substrate 110 is not particularly limited and can be appropriately chosen from known resins. Examples of the resin configuring first substrate 110 include polyethylene terephthalate, polycarbonate, polymethylmethacrylate, vinyl chloride, polypropylene, polyether and polyethylene.

As shown in FIGS. 2A to 2C, first channel 111, second channel 112, first fluid introduction port 113, valve body facing area 114, partition wall 115, and fluid outlet port 116 are formed in first substrate 110. First channel 111, valve body facing area 114, and second channel 112 function as a single channel, and thus a fluid introduced from first fluid introduction port 113 can flow to fluid outlet port 116 while the microvalve opens.

First channel 111 and second channel 112 are channels in which a fluid (e.g.; a reagent, a liquid sample) introduced from first fluid introduction port 113 flows. First channel 111 and second channel 112 are grooves formed in first substrate 110. Openings of these grooves are blocked by resin film 130 (refer to FIG. 1B). The cross-sectional areas and the cross-sectional shapes of first channel 111 and second channel 112 are not particularly limited. For example, first channel 111 and second channel 112 are channels in which a fluid can move by capillary action. In this case, the cross-sectional shape of each of first channel 111 and second channel 112 is, for example, a substantially rectangular shape in which the dimension (width or depth) of one side is on the order of several tens of μm. As used herein, "cross section of a channel" means the cross section of a channel orthogonal to a direction in which a fluid flows.

First fluid introduction port 113 and fluid outlet port 116 are through-holes formed in first substrate 110. First fluid introduction port 113 is formed at a first end (an end upstream) of first channel 111. Further, fluid outlet port 116 is formed at a second end (an end downstream) of second channel 112. Openings on one side of these through-holes are blocked by resin film 130 (refer to FIG. 1B). The shapes of first fluid introduction port 113 and fluid outlet port 116 are not particularly limited. The shape is, for example, a substantially columnar shape. The diameters of first fluid introduction port 113 and fluid outlet port 116 are not particularly limited. The diameter is, for example, about 2 mm.

Valve body facing area 114 is a recess formed in first substrate 110. Valve body facing area 114 is formed at a second end (an end downstream) of first channel 111. An opening of the recess faces resin film 130 (a diaphragm portion 131) (refer to FIG. 1B). The shape of an opening on the resin film 130 side of valve body facing area 114 is a substantially circular shape (refer to FIGS. 2A and 5). The shape of valve body facing area 114 is not particularly limited as long as the shape of the opening is a substantially circular shape. The shape of valve body facing area 114 is, for example, a columnar shape. The diameter of the opening of valve body facing area 114 is not particularly limited. The diameter is, for example, about 0.5 mm.

Partition wall 115 is a wall formed between first channel 111 and a first end (an end upstream) of second channel 112. As will be described later, partition wall 115 functions as a valve seat of the microvalve.

(Second Substrate)

FIGS. 3A to 3C are diagrams showing the configuration of second substrate 120. FIG. 3A is a plan view of second substrate 120, FIG. 3B is a cross-sectional view taken along line B-B shown in FIG. 3A, and FIG. 3C is a cross-sectional view taken along line C-C shown in FIG. 3A.

Second substrate 120 is a substantially rectangular transparent resin substrate. The thickness of second substrate 120 is not particularly limited. The thickness is, for example, in a range of 1 mm to 10 mm. The type of resin configuring second substrate 120 is not particularly limited and can be appropriately chosen from known resins. An example of the resin configuring second substrate 120 is the same as an example of the resin configuring first substrate 110.

As shown in FIGS. 3A to 3C, third channel 121, second fluid introduction port 122, and pressure chamber 123 are formed in second substrate 120.

Third channel 121 is a channel in which a fluid (e.g.; air) introduced from second fluid introduction port 122 flows. Third channel 121 is a groove formed in second substrate 120. An opening of the groove is blocked by resin film 130 (refer to FIG. 1C). The cross-sectional area and the cross-sectional shape of third channel 121 are not particularly limited. For example, the cross-sectional shape of third channel 121 is a substantially rectangular shape in which, for example, the dimension (width or depth) of one side is on the order of several tens of µm.

Second fluid introduction port 122 is a through-hole formed in second substrate 120. Second fluid introduction port 122 is formed at a first end (an end upstream) of third channel 121. An opening on one side of the through-hole is blocked by resin film 130 (refer to FIG. 1C). The shape of second fluid introduction port 122 is not particularly limited. The shape is, for example, a substantially columnar shape. The diameter of second fluid introduction port 122 is not particularly limited. The diameter is, for example, about 2 mm.

Pressure chamber 123 is a recess formed in second substrate 120. Pressure chamber 123 is formed at a second end (an end downstream) of third channel 121. An opening of the recess is blocked by resin film 130 (refer to FIG. 1C). The shape of an opening of pressure chamber 123 on the resin film 130 side is not particularly limited as long as the opening is the same size as or larger than diaphragm portion 131 of resin film 130, and is, for example, a substantially circular shape (refer to FIGS. 3A and 5). The shape of pressure chamber 123 is not particularly limited. The shape is, for example, a columnar shape. The diameter of the opening of pressure chamber 123 is not particularly limited. The diameter is, for example, about 1 mm.

(Resin Film)

Figures 4A, 4B:
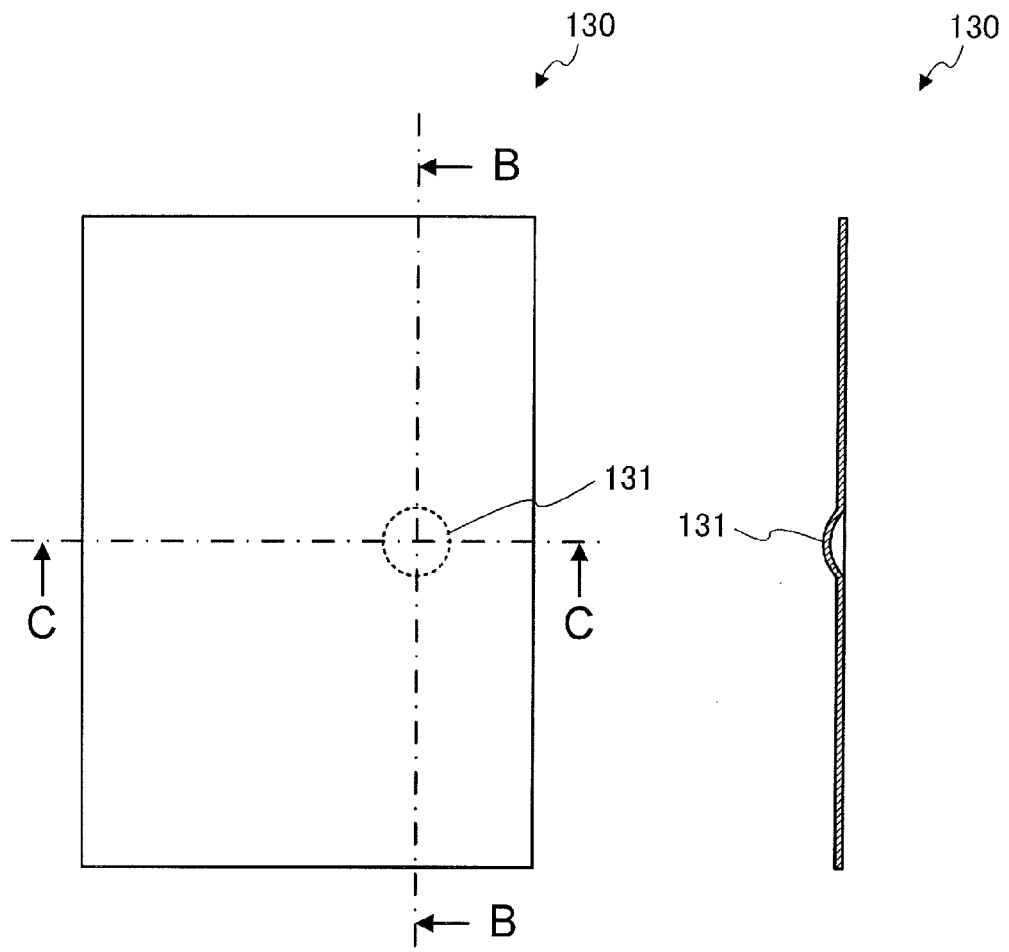
FIG. 4A is a plan view of a resin film.
FIG. 4B is a cross-sectional view taken along line B-B shown in FIG. 4A.
Figure 4C:
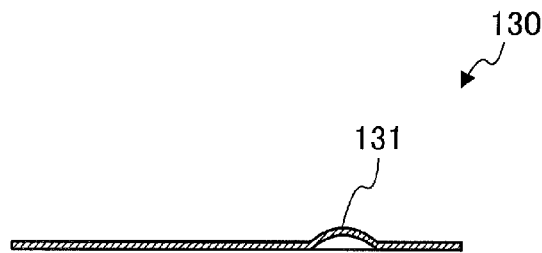
FIG. 4C is a cross-sectional view taken along line C-C shown in FIG. 4A.

FIGS. 4A to 4C are diagrams showing the configuration of resin film 130. FIG. 4A is a plan view of resin film 130, FIG. 4B is a cross-sectional view taken along line B-B shown in FIG. 4A, and FIG. 4C is a cross-sectional view taken along line C-C shown in FIG. 4A.

Resin film 130 is a substantially rectangular transparent resin film. Resin film 130 functions as a valve body (a diaphragm) of a microvalve having a diaphragm structure.

A first surface of resin film 130 is joined to the surface of first substrate 110 where first channel 111 and the like formed. Further, a second surface of resin film 130 is joined to the surface of second substrate 120 where third channel 121 and the like formed (refer to FIGS. 1A to 1C). As described above, resin film 130 blocks the openings of first channel 111, second channel 112, first fluid introduction port 113, and fluid outlet port 116 formed in first substrate 110 and the openings of third channel 121, second fluid introduction port 122, and pressure chamber 123 formed in second substrate 120.

The type of resin configuring resin film 130 is not particularly limited as long as resin film 130 can function as a valve body (a diaphragm), and can be appropriately chosen from known resins. An example of the resin configuring resin film 130 is the same as the example of the resin configuring first substrate 110. From the perspective of improving adhesion between resin film 130 and first and second substrates 110 and 120, it is preferable that the resin configuring resin film 130 be the same as the resin configuring first substrate 110 and second substrate 120.

The thickness of resin film 130 is not particularly limited as long as resin film 130 can function as a valve body (a diaphragm), and can be appropriately set according to the type (rigidity) of resin. For example, the thickness of resin film 130 is about 20 µm.

As shown in FIGS. 4A to 4C, resin film 130 includes substantially spherical cap-shaped diaphragm portion 131. As shown in FIG. 1B, valve body facing area 114, partition wall 115, and the first end (the end upstream) of second channel 112 of first substrate 110 and pressure chamber 123 of second substrate 120 face each other with resin film 130 interposed therebetween. The portion which is located between the opening of valve body facing area 114, partition wall 115, and the first end (the end upstream) of second channel 112, and the opening of pressure chamber 123, of resin film 130, is diaphragm portion 131. Diaphragm portion 131 has a substantially spherical cap shape and is not joined to first substrate 110 and second substrate 120.

As shown in FIGS. 4B and 4C, diaphragm portion 131 is deformed so as to form a protruding shape toward pressure chamber 123. For this reason, when pressure in pressure chamber 123 is not increased, diaphragm portion 131 does not come into contact with partition wall 115 of first substrate 110. The height of diaphragm portion 131 in a normal state is not particularly limited as long as a fluid can flow through a gap which is formed between diaphragm portion 131 and partition wall 115. For example, the height of diaphragm portion 131 is on the order of several tens of µm.

Figure 5:
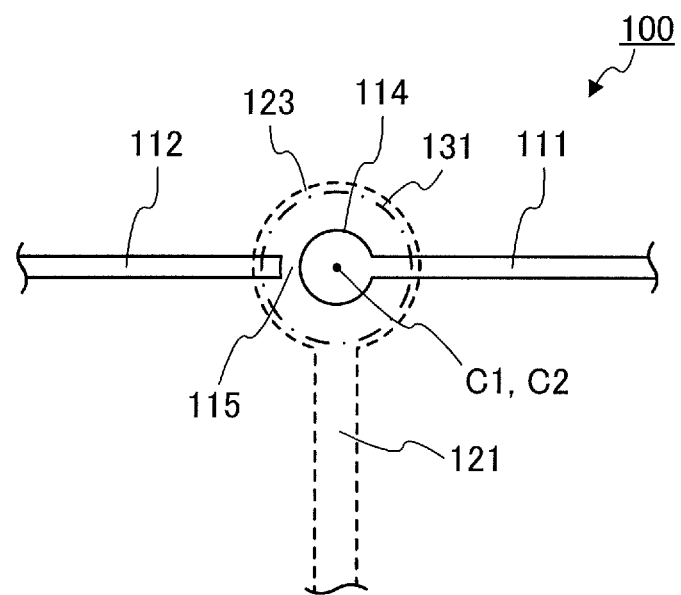
FIG. 5 is a partially enlarged plan view of the microchannel chip according to Embodiment 1.

FIG. 5 is a partially enlarged plan view of the microchannel chip 100. In this drawing, constituent elements formed in first substrate 110 are shown by solid lines, constituent elements formed in second substrate 120 are shown by dashed lines, and a constituent element formed in resin film 130 is shown by a dashed-dotted line. As described above, the shape of the opening on the resin film 130 side of valve body facing area 114 formed in first substrate 110 is a substantially circular shape. Further, the shape of diaphragm portion 131 of resin film 130 is a substantially spherical cap shape. Since diaphragm portion 131 faces not only valve body facing area 114, but also partition wall 115 and the first end (the end upstream) of second channel 112, diaphragm portion 131 is larger than the substantially circular opening of valve body facing area 114. On the other hand, diaphragm portion 131 is the same size as or smaller than the opening of pressure chamber 123.

Figure 6:
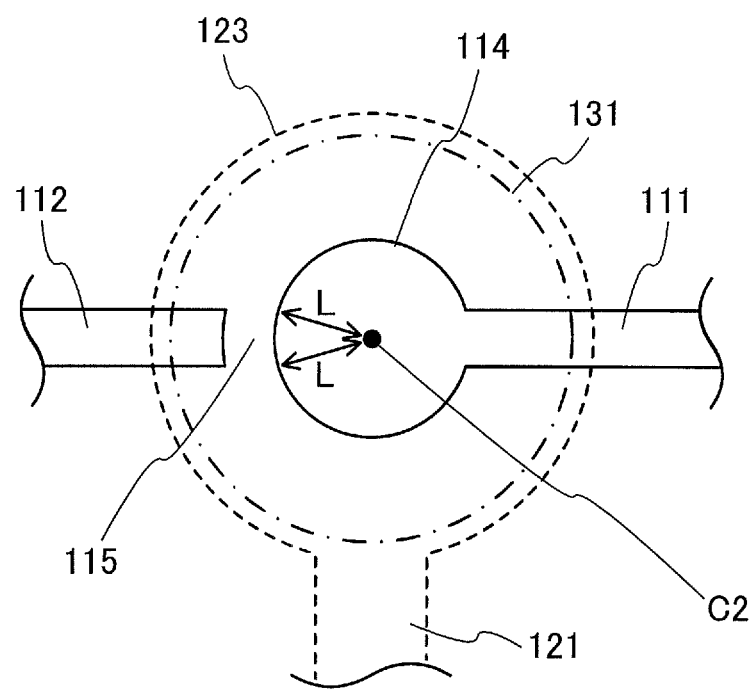
FIG. 6 is a partially enlarged plan view of the microchannel chip according to Embodiment 1.

As shown in FIG. 5, when microchannel chip 100 is viewed in a plan view, center C1 of the substantially circular opening of valve body facing area 114 coincides with center C2 of an outer edge of substantially spherical cap-shaped diaphragm portion 131. That is, an edge of the opening of valve body facing area 114 and the outer edge of diaphragm portion 131 of resin film 130 are concentric circles. By doing so, as shown in FIG. 6, distance L from center C2 of diaphragm portion 131 to partition wall 115 becomes constant (the same distance as the radius of valve body facing area 114).

In addition, in the example shown in FIGS. 1A to 1C, 5, and 6, an aspect is shown in which the sizes of diaphragm portion 131 and the opening of pressure chamber 123 almost coincide with each other. However, the invention is not limited thereto, and the size of diaphragm portion 131 is not particularly limited as long as diaphragm portion 131 is located in the opening of pressure chamber 123 and formed so as to function as a diaphragm for opening and closing a communication portion between first channel 111 and second channel 112. That is, the size of diaphragm portion 131 may be the same size as or smaller than the opening of pressure chamber 123.

Microchannel chip 100 according to the present embodiment is manufactured, for example, by joining first substrate 110 shown in FIGS. 2A to 2C, second substrate 120 shown in FIGS. 3A to 3C, and resin film 130 (or flat resin film 130) shown in FIGS. 4A to 4C. For example, resin film 130 is joined to first substrate 110 and second substrate 120 by thermocompression bonding with various conditions adjusted.

[How to Use Microchannel Chip]

Figure 7A:
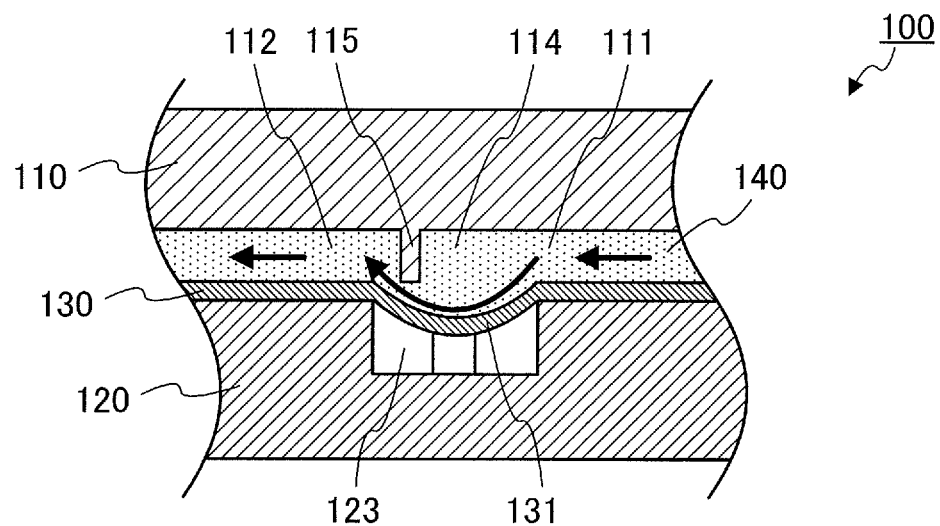
FIGS. 7A and 7B are partially enlarged cross-sectional views of the microchannel chip according to Embodiment 1 for describing how the microchannel chip is used.
Figure 7B:
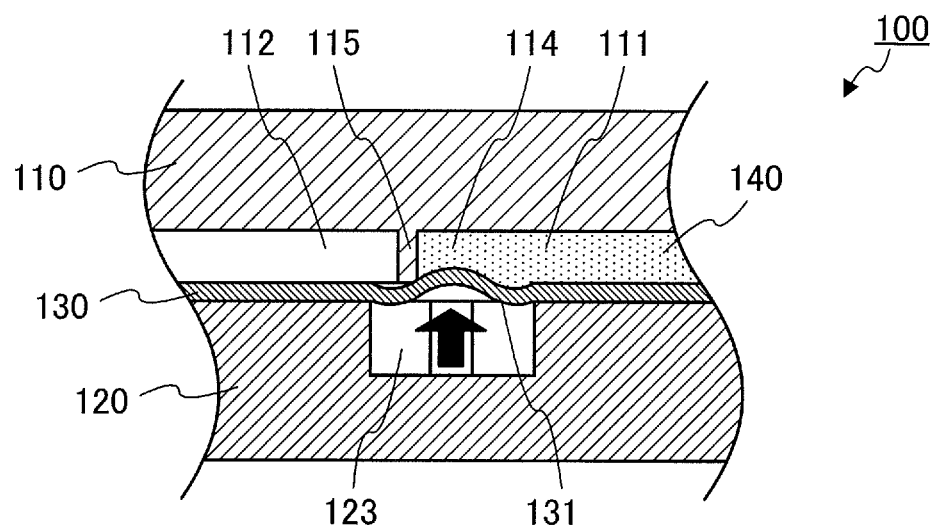

Next, how to use microchannel chip 100 according to the present embodiment will be described with reference to FIGS. 7A and 7B. FIGS. 7A and 7B are partially enlarged cross-sectional views (corresponding to FIG. 1B) of microchannel chip 100 for describing how microchannel chip 100 is used.

First, as shown in FIG. 7A, liquid 140 such as a reagent or a liquid sample is introduced into first channel 111 by supplying liquid 140 into first fluid introduction port 113. At this time, pressure in pressure chamber 123 is not increased and thus a gap is formed between resin film 130 (diaphragm portion 131) and partition wall 115 (a valve open state). Liquid 140 advances through first channel 111, the gap between partition wall 115 and resin film 130 (diaphragm portion 131), and second channel 112 by capillary action or pressure from the outside and reaches fluid outlet port 116. In addition, a fluid (a first fluid) which is introduced from first fluid introduction port 113 need not be liquid and may be gas.

Subsequently, as shown in FIG. 7B, air is introduced from second fluid introduction port 122 into pressure chamber 123 through third channel 121. As a result, pressure in pressure chamber 123 increases, and thus the shape of resin film 130 (diaphragm portion 131) changes. Specifically, diaphragm portion 131 turns into a protruding shape toward the valve body facing area 114 side. In this way, resin film 130 (diaphragm portion 131) comes into contact with partition wall 115 (a valve close state). Liquid 140 cannot advance between partition wall 115 and resin film 130 (diaphragm portion 131) and the flow of liquid 140 stops. In addition, a fluid (a second fluid) which is introduced from second fluid introduction port 122 need not be air and may be liquid or gas other than air.

When diaphragm portion 131 turns into the protruding shape toward the valve body facing area 114 side, since the shape of diaphragm portion 131 is a substantially circular shape, the heights of the respective points of diaphragm portion 131 change concentrically. That is, when the distances from the center of diaphragm portion 131 are the same, heights are also the same. As described above, in microchannel chip 100 according to the present embodiment, distance L from the center of diaphragm portion 131 to partition wall 115 is constant (the same distance as the radius of valve body facing area 114) (refer to FIG. 6). Therefore, when diaphragm portion 131 turns into the protruding shape toward the valve body facing area 114 side, diaphragm portion 131 uniformly comes into contact with partition wall 115. As a result, in microchannel chip 100 according to the present embodiment, even if pressure in pressure chamber 123 is not excessively increased, it is possible to reliably stop the flow of liquid 140 in first channel 111.

By the above procedure, allowing liquid 140 to flow from first channel 111 to second channel 112 and stopping the flow of liquid 140 from first channel 111 to second channel 112 can be performed at any timing. For example, it is possible to allow liquid 140 to react with a specific reagent in first fluid introduction port 113 for a given length of time, thereafter, moving liquid 140 in first fluid introduction port 113 into fluid outlet port 116, and react liquid 140 with another reagent in fluid outlet port 116.

[Effects]

Microchannel chip 100 according to the present embodiment allows easy control of the fluid (a first fluid) flow flowing from first channel 111 to second channel 112, by adjusting the pressure of a fluid (a second fluid) in pressure chamber 123. Further, since microchannel chip 100 according to the present embodiment can be manufactured using resin, rather than an elastomer, it is possible to suppress manufacturing costs. In this manner, in microchannel chip 100 according to the present embodiment, a manufacturing cost is low and it is possible to easily control the fluid flow in a channel.

Figure 8:
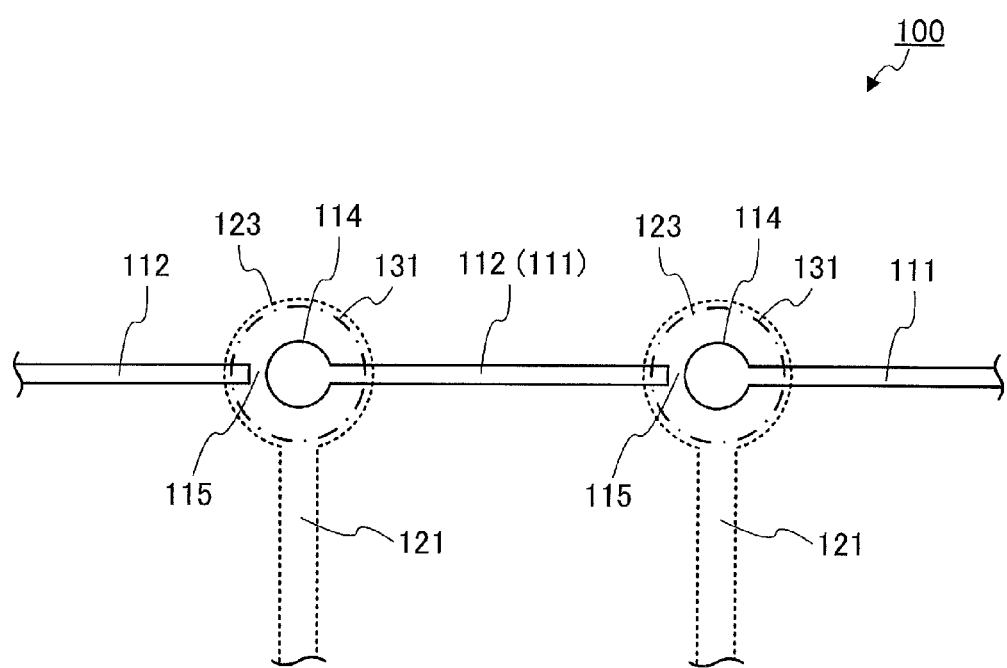
FIG. 8 is a partially enlarged plan view showing another example of the microchannel chip according to Embodiment 1.

In addition, in the description so far, microchannel chip 100 has been described in which one microvalve structure which includes valve body facing area 114, partition wall 115, and pressure chamber 123 is formed. However, the number of microvalve structures in microchannel chip 100 is not limited thereto. For example, as shown in FIG. 8, a plurality of microvalve structures may be formed in single microchannel chip 100.

Embodiment 2

Configuration of Microchannel Chip

Figure 9:
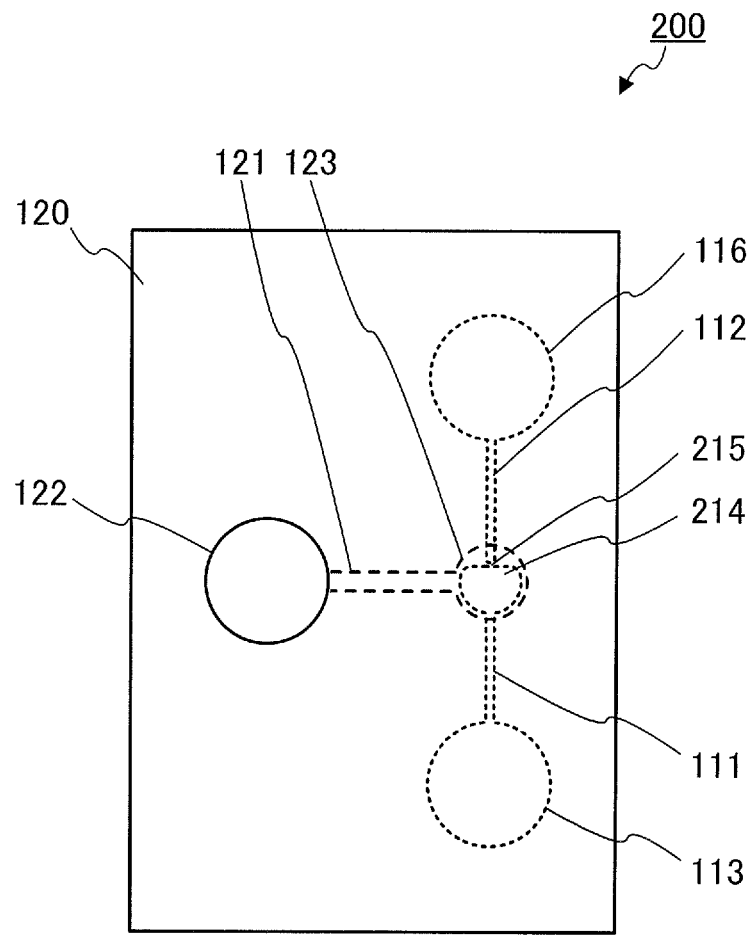
FIG. 9 is a plan view of a microchannel chip according to Embodiment 2.

FIG. 9 is a plan view showing the configuration of microchannel chip 200 according to Embodiment 2. Microchannel chip 200 has, similar to microchannel chip 100 according to Embodiment 1, first substrate 210, second substrate 120, and resin film 130 disposed between first substrate 210 and second substrate 120 (refer to FIGS. 12A and 12B).

Figure 10C:
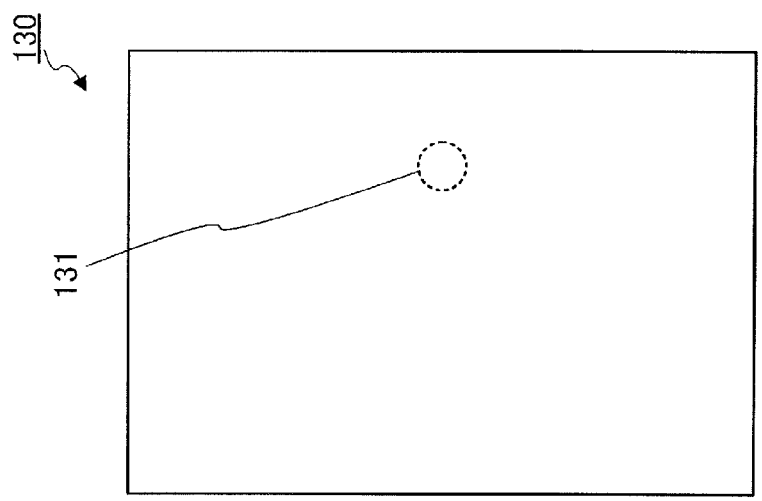
FIG. 10C is a plan view of a resin film.
Figure 10B:
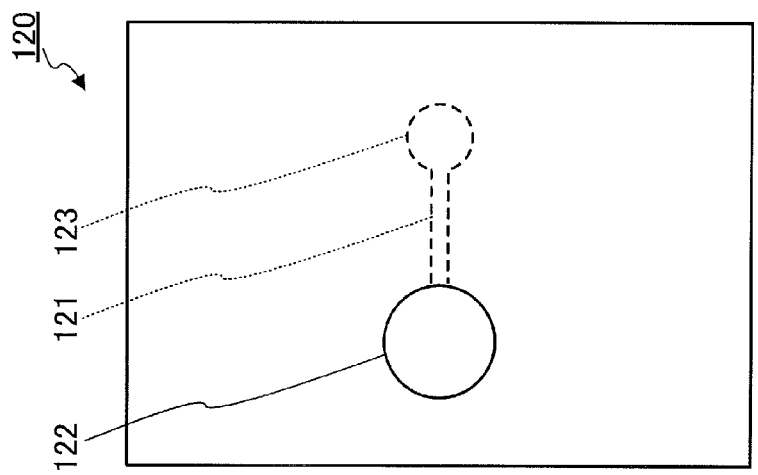
FIG. 10B is a plan view of a second substrate.
Figure 10A:
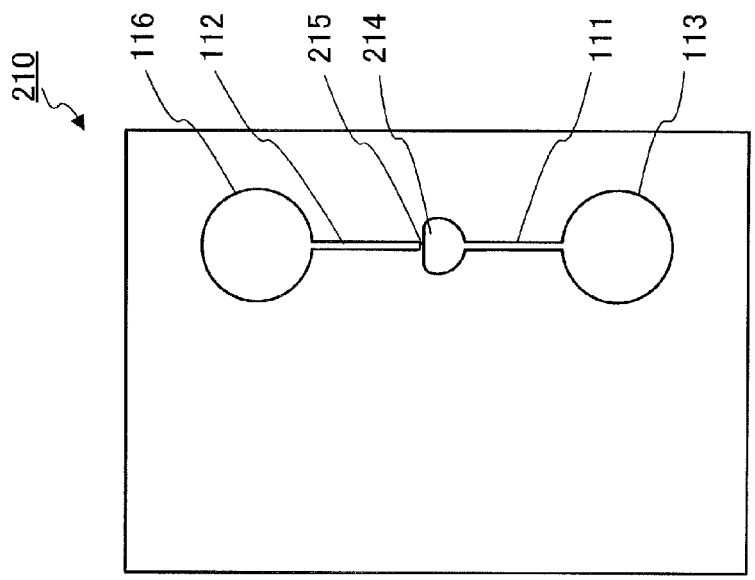
FIG. 10A is a plan view of a first substrate.

FIG. 10A is a plan view of first substrate 210, FIG. 10B is a plan view of second substrate 120, and FIG. 10C is a plan view of resin film 130. Similar to microchannel chip 100 according to Embodiment 1, first substrate 210 and second substrate 120 are integrated with each other through resin film 130 (refer to FIGS. 12A and 12B).

In microchannel chip 200 according to Embodiment 2, the shapes of valve body facing area 214 and partition wall 215 provided in first substrate 210 are different from those in microchannel chip 100 according to Embodiment 1. Therefore, in the present embodiment, only first substrate 210 will be described. The same constituent elements as those in microchannel chip 100 according to Embodiment 1 are denoted by the same reference numerals and description thereof is omitted.

As shown in FIG. 10A, first channel 111, second channel 112, first fluid introduction port 113, valve body facing area 214, partition wall 215, fluid outlet port 116 are formed in first substrate 210. First channel 111, valve body facing area 214, and second channel 112 function as a single channel, and thus a fluid introduced from first fluid introduction port 113 can flow to fluid outlet port 116 while the microvalve opens.

Valve body facing area 214 is a recess formed in first substrate 210. Valve body facing area 214 is formed at a second end (an end downstream) of first channel 111. An opening of the recess faces resin film 130 (diaphragm portion 131) (refer to FIGS. 12A and 12B). The shape of an opening on the resin film 130 side of valve body facing area 214 is an approximate circular segment (refer to FIG. 10A). As used herein, "circular segment" refers to a shape which is obtained when a circle is divided into two by a single chord. The circular segment includes a single circular arc and a single chord connecting both ends of the circular arc. The shape of valve body facing area 214 is not particularly limited as long as the shape of the opening is an approximate circular segment. For example, the valve body facing area 214 has a columnar shape whose bases are circular segments.

Partition wall 215 is a wall formed between valve body facing area 214 (a chord portion of the circular segment) and a first end (an end upstream) of second channel 112. Partition wall 215 functions as a valve seat of a microvalve.

Figure 11:
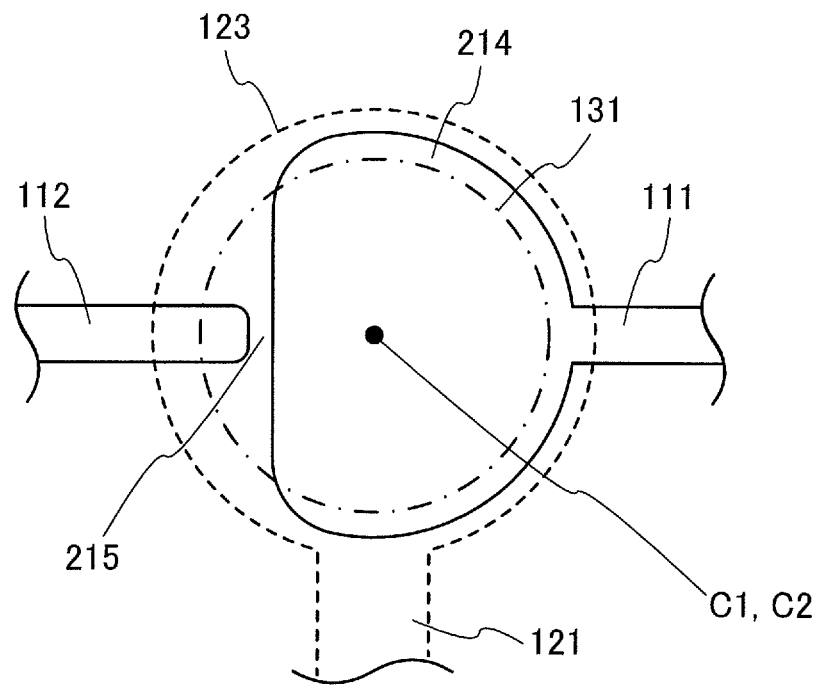
FIG. 11 is a partially enlarged plan view of the microchannel chip according to Embodiment 2.

FIG. 11 is a partially enlarged plan view of microchannel chip 200. In this drawing, constituent elements formed in first substrate 210 are shown by solid lines, constituent elements formed in second substrate 120 are shown by dashed lines, and a constituent element formed in resin film 130 is shown by a dashed-dotted line. As described above, the shape of the opening on the resin film 130 side of valve body facing area 214 formed in first substrate 210 is an approximate circular segment. The shape of diaphragm portion 131 of resin film 130 is a substantially spherical cap shape.

As shown in FIG. 11, when microchannel chip 200 is viewed in a plan view, center C1 of the circular arc which is a portion of an edge of the approximately circular segment-shaped opening of valve body facing area 214 coincides with center C2 of an outer edge of substantially spherical cap-shaped diaphragm portion 131. Further, the radius of the outer edge of diaphragm portion 131 is smaller than the radius (the distance between center C1 and the circular arc) of the circular arc of valve body facing area 214. By doing so, as shown in FIG. 11, the distance from the edge (a circular arc portion) of the opening of valve body facing area 214 to the outer edge of diaphragm portion 131 becomes constant. In addition, as long as the distance from the edge (the circular arc portion) of the opening of valve body facing area 214 to the outer edge of diaphragm portion 131 is constant, the radius of the outer edge of diaphragm portion 131 may be equal to or slightly larger than the radius (the distance between center C1 and the circular arc) of the circular arc of valve body facing area 214. Resin film 130 between the edge (the circular arc portion) of the opening of valve body facing area 214 and the outer edge of diaphragm portion 131 has a flat plate shape (refer to FIGS. 12A and 12B).

In addition, even when the radius of the outer edge of diaphragm portion 131 is smaller than the radius of the circular arc of valve body facing area 214, since the shape of the opening of valve body facing area 214 is an approximate circular segment, diaphragm portion 131 can face not only valve body facing area 214, but also partition wall 215 and the first end (the end upstream) of second channel 112.

Microchannel chip 200 according to the present embodiment can be manufactured, for example, by joining first substrate 210 shown in FIG. 10A, second substrate 120 shown in FIG. 10B, and resin film 130 shown in FIG. 10C to each other. For example, resin film 130 is joined to first substrate 210 and second substrate 120 by thermocompression bonding with various conditions adjusted.

[How to Use Microchannel Chip]

Figure 12A:
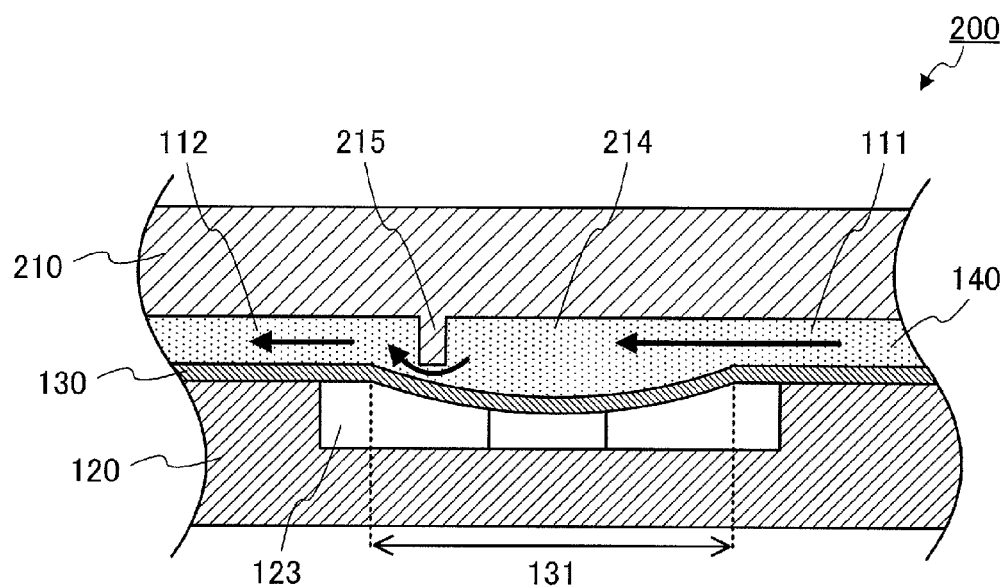
FIGS. 12A and 12B are partially enlarged cross-sectional views of the microchannel chip according to Embodiment 2 for describing how the microchannel chip is used.
Figure 12B:
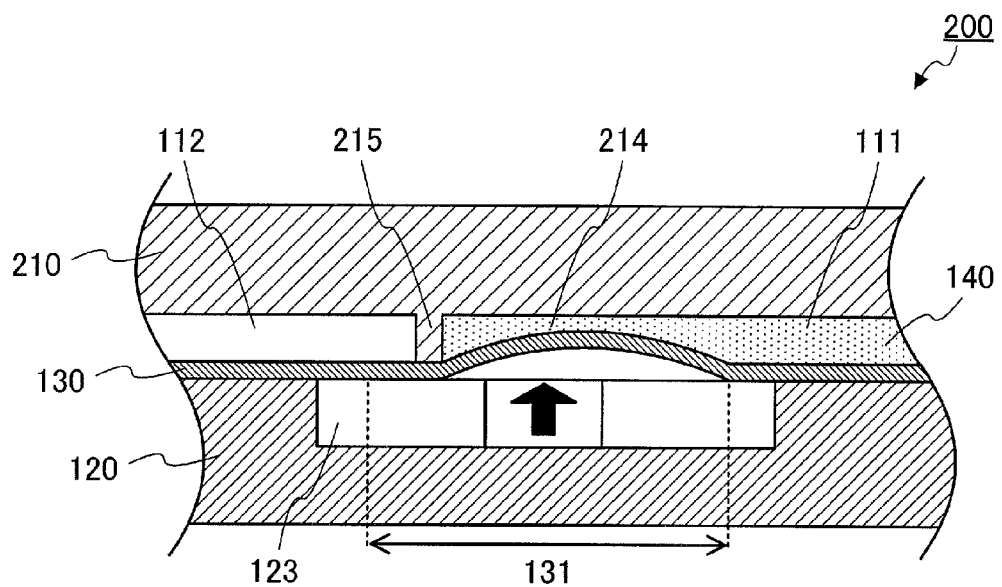

Next, how to use microchannel chip 200 according to the present embodiment will be described with reference to FIGS. 12A and 12B. FIGS. 12A and 12B are partially enlarged cross-sectional views of microchannel chip 200 for describing how microchannel chip 200 is used.

First, as shown in FIG. 12A, liquid 140 such as a reagent or a liquid sample is introduced into first channel 111 by supplying liquid 140 into first fluid introduction port 113. At this time, pressure in pressure chamber 123 is not increased and thus a gap is formed between resin film 130 (diaphragm portion 131) and partition wall 215 (a valve open state). Liquid 140 advances through first channel 111, the gap between partition wall 215 and resin film 130 (diaphragm portion 131), and second channel 112 by capillary action or pressure from the outside and reaches fluid outlet port 116. In addition, a fluid (a first fluid) which is introduced from first fluid introduction port 113 need not be liquid and may be gas.

Subsequently, as shown in FIG. 12B, air is introduced from second fluid introduction port 122 into pressure chamber 123 through third channel 121. As a result, pressure in pressure chamber 123 increases, and thus the shape of resin film 130 (diaphragm portion 131) changes. Specifically, diaphragm portion 131 turns into a protruding shape toward the valve body facing area 214 side. In this way, resin film 130 (diaphragm portion 131) comes into contact with partition wall 215 (a valve close state). Liquid 140 cannot advance between partition wall 215 and resin film 130 (diaphragm portion 131) and the flow of liquid 140 stops. In addition, a fluid (a second fluid) which is introduced from second fluid introduction port 122 need not be air and may be liquid or gas other than air.

In microchannel chip 200 according to the present embodiment, since the radius of the outer edge of diaphragm portion 131 is smaller than the radius of the circular arc of valve body facing area 214, it is difficult for a gap to be formed between diaphragm portion 131 and partition wall 215 (refer to FIG. 12B by comparing with FIG. 7B). Therefore, when diaphragm portion 131 turns into the protruding shape toward the valve body facing area 214 side, diaphragm portion 131 uniformly comes into contact with partition wall 215. As a result, in microchannel chip 200 according to the present embodiment, even if pressure in pressure chamber 123 is not excessively increased, it is possible to reliably stop the flow of liquid 140 in first channel 111.

By the above procedure, allowing liquid 140 to flow from first channel 111 to second channel 112 and stopping the flow of liquid 140 from first channel 111 to second channel 112 can be performed at any timing.

[Effects]

Microchannel chip 200 according to the present embodiment has the effects that it is difficult for air bubbles to enter between diaphragm portion 131 and partition wall 215 and therefore easier to handle microchannel chip 200, in addition to the same effects as those of microchannel chip 100 according to Embodiment 1.

Figure 13:
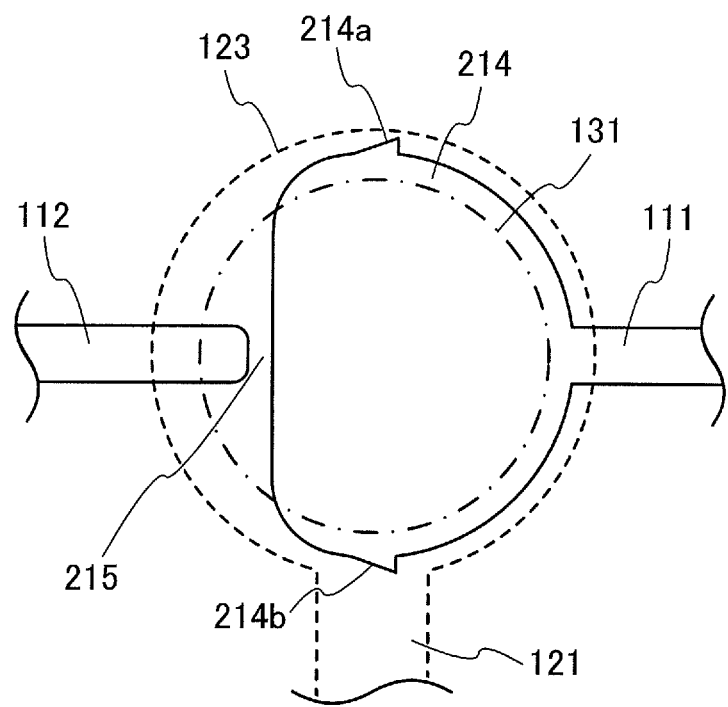
FIG. 13 is a partially enlarged plan view showing another example of the microchannel chip according to Embodiment 2.

In addition, as shown in FIG. 13, two or more protruding stripes or recessed stripes 214a and 214b extending in a direction perpendicular to resin film 130 may be formed in a side wall configuring valve body facing area 214. In this case, it is preferable that the two or more protruding stripes or recessed stripes 214a and 214b be disposed symmetrically with respect to an opening of first channel 111. By doing so, it becomes possible to make liquid 140 passing through a central portion in valve body facing area 214 preferentially flow, and thus it becomes more difficult for air bubbles to enter between diaphragm portion 131 and partition wall 215.

This application claims the right of priority based on Japanese Patent Application No. 2011-161914 filed on Jul. 25, 2011 and Japanese Patent Application No. 2012-160407 filed on Jul. 19, 2012. The entire contents described in the specifications and the drawings of the applications are incorporated herein by reference.

INDUSTRIAL APPLICABILITY

The fluid handling device according to the invention is useful as a microchip or a microchannel chip which is used in, for example, a scientific field, a medical field, or the like.

REFERENCE SIGNS LIST 100, 200 Microchannel chip
110, 210 First substrate
111 First channel
112 Second channel
113 First fluid introduction port
114, 214 Valve body facing area
115, 215 Partition wall
116 Fluid outlet port
120 Second substrate
121 Third channel
122 Second fluid introduction port
123 Pressure chamber
130 Resin film
131 Diaphragm portion
140 Liquid
214a, 214b Recessed stripe

The invention claimed is:

1. A fluid handling device comprising:
a first substrate which includes a first channel, a valve body facing area formed at an end on one side of the first channel and having a substantially circular segment-shaped opening, a second channel, and a partition wall formed between the valve body facing area and an end on one side of the second channel;
a second substrate which includes a third channel and a pressure chamber, the pressure chamber being formed at an end on one side of the third channel and having an opening; and
a resin film which is disposed between the first substrate and the second substrate and includes a substantially spherical cap-shaped diaphragm portion,
wherein the first substrate and the second substrate are integrated with each other with the resin film in between,
the diaphragm portion is located between the opening of the valve body facing area, the end on one side of the second channel and the partition wall, and the opening of the pressure chamber,
a center of a circular arc which is included in an edge of the opening of the valve body facing area and a center of an outer edge of the diaphragm portion coincide with each other when seen in a plan view,
the diaphragm portion comes into contact with the partition wall due to pressure in the pressure chamber, whereby fluid flow heading for the second channel from the valve body facing area through a gap between the partition wall and the diaphragm portion is stopped,
two or more protruding stripes or recessed stripes extending in a direction perpendicular to the resin film are formed in a side wall configuring the valve body facing area, and
the two or more protruding stripes or recessed stripes are disposed symmetrically with respect to an opening of the first channel.

2. The fluid handling device according to claim 1, wherein a radius of the outer edge of the diaphragm portion is smaller than a radius of the circular arc of the valve body facing area.

3. A method of handling a fluid by using the fluid handling device according to claim 2, comprising:
introducing a first fluid into the first channel to move the first fluid from the first channel through a gap between the partition wall and the diaphragm portion to the second channel; and
stopping the first fluid flow by introducing a second fluid into the pressure chamber through the third channel and thus bringing the diaphragm portion into contact with the partition wall due to pressure of the second fluid in the pressure chamber.

4. A method of handling a fluid by using the fluid handling device according to claim 1, comprising:
introducing a first fluid into the first channel to move the first fluid from the first channel through a gap between the partition wall and the diaphragm portion to the second channel; and
stopping the first fluid flow by introducing a second fluid into the pressure chamber through the third channel and thus bringing the diaphragm portion into contact with the partition wall due to pressure of the second fluid in the pressure chamber.

5. A fluid handling device comprising:
a first substrate which includes a first channel, a valve body facing area formed at an end on one side of the first channel and having a substantially circular opening, a second channel, and a partition wall formed between the valve body facing area and an end on one side of the second channel;
a second substrate which includes a third channel and a pressure chamber, the pressure chamber being formed at an end on one side of the third channel and having an opening; and
a resin film which is disposed between the first substrate and the second substrate and includes a substantially spherical cap-shaped diaphragm portion,
wherein the first substrate and the second substrate are integrated with each other with the resin film in between,
the diaphragm portion is located between the opening of the valve body facing area, the end on one side of the second channel and the partition wall, and the opening of the pressure chamber,
when seen in a plan view, the diaphragm portion is larger than the opening of the valve body facing area and an edge of the opening of the valve body facing area and an outer edge of the diaphragm portion of the resin film are concentric circles,
the diaphragm portion comes into contact with the partition wall due to pressure in the pressure chamber, whereby fluid flow heading for the second channel from the valve body facing area through a gap between the partition wall and the diaphragm portion is stopped, two or more protruding stripes or recessed stripes extending in a direction perpendicular to the resin film are formed in a side wall configuring the valve body facing area, and the two or more protruding stripes or recessed stripes are disposed symmetrically with respect to an opening of the first channel.

6. A method of handling a fluid by using the fluid handling device according to claim 5, comprising:

introducing a first fluid into the first channel to move the first fluid from the first channel through a gap between the partition wall and the diaphragm portion to the second channel; and stopping the first fluid flow by introducing a second fluid into the pressure chamber through the third channel and thus bringing the diaphragm portion into contact with the partition wall due to pressure of the second fluid in the pressure chamber.

* * * * *